(12) United States Patent
Huang et al.

(10) Patent No.: US 8,663,967 B2
(45) Date of Patent: Mar. 4, 2014

(54) ARGININE DEIMINASE MUTANT AND PREPARATION AND APPLICATION THEREOF

(75) Inventors: Yanshan Huang, China Medical (CN); Jiwan Qiu, China Medical (CN); Xiaoyu Fu, China Medical (CN); Min Fan, China Medical (CN); Yujiao Wang, China Medical (CN); Yefei Wang, China Medical (CN)

(73) Assignee: Jiangsu T-MAB Biopharma Co., Ltd., Jiangsu Province (CN)

( * ) Notice: Subject to any disclaimer, the term of this patent is extended or adjusted under 35 U.S.C. 154(b) by 175 days.

(21) Appl. No.: 13/214,398

(22) Filed: Aug. 22, 2011

(65) Prior Publication Data
US 2013/0052179 A1 Feb. 28, 2013

(51) Int. Cl.
| | | |
|---|---|---|
| *C12N 11/02* | (2006.01) | |
| *C12N 11/08* | (2006.01) | |
| *C12N 9/00* | (2006.01) | |
| *C12N 9/78* | (2006.01) | |
| *C12N 1/20* | (2006.01) | |
| *C12N 15/00* | (2006.01) | |
| *C07H 21/04* | (2006.01) | |

(52) U.S. Cl.
USPC ........... 435/227; 435/177; 435/180; 435/183; 435/252.3; 435/320.1; 536/23.2

(58) Field of Classification Search
None
See application file for complete search history.

(56) References Cited

PUBLICATIONS

Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — Ming Chow; Sinorica, LLC

(57) ABSTRACT

The present invention relates to an arginine deiminase mutant with partial lysine-deficient and preparation and application thereof. The arginine deiminase mutant of the present invention has enzymatic activity of degrading arginine into citruline; compared with the arginine deiminase with the amino acid sequence of SEQ ID NO: 1, the amino acid sequence comprises one or more of K9N, T, K59Q, K66R, A, K93E, A, Q, K111R, A, K119Q, L, M, K121Q, I, K122E, L, K126E, S, R, K178I, E, D, K196I, R, K209G, T, D, K243E, V, R, K249D, Q, K263N, Q, K279Y, T, K293R, H, E, K325V, I, K380T, R, E, and K406E, D, S substitutions. Compared with PEG modified natural derived arginine deiminase, the PEG modified arginine deiminase mutant of the present invention retain better bioactivity; and because the quantity of lysine in arginine deiminase is reduced, the PEG modified products are more uniform and can be applied to clinical treatment of hepatoma, melanoma and the like.

9 Claims, 3 Drawing Sheets

ARGININE DEIMINASE MUTANT AND PREPARATION AND APPLICATION THEREOF

FIELD OF THE INVENTION

The present invention relates to the field of biotechnology, and more particularly, to an arginine deiminase mutant and preparation and application thereof.

BACKGROUND OF THE INVENTION

Arginine, which is one of essential amino acids for the cell growth of many species, could be synthesized from citrulline in the normal cells through a two-step reaction catalyzed by argininosuccinate synthetase (ASS) and argininosuccinate lyase (AL) shown as following: L-arginine+$H_2O$ ⇌ L-citrulline+$NH_3$. Therefore, normal cells don't require external supply of arginine for growth. However, the nature of arginine auxotrophy appears in some abnormal appearing cells, such as hepatocellular carcinomas (HCC), melanoma or other sarcomas, within which arginine could not be synthesized because of lack of ASS in these cells. Therefore, these kinds of abnormal appearing cells could be survived only in the environment containing arginine which is the main essential amino acid required in the growth of these abnormal cells. In the presence of enzymes for degradation of arginine, the arginine existing in the environment could be eliminated which will result in starvation of these abnormal cells whose growth will be significantly inhibited. Therefore, the arginine-degrading enzyme can be used as a potential clinical drug for liver cancer, melanoma and other diseases. Arginine deiminase (ADI), which catalyzes the conversion of arginine to citrulline, could be used for eliminating arginine. The pADI isolated from *Pseudomonas putida* could effectively kill the tumor cells in vitro (Jones J B, The effect of arginine deiminase on murine leukemia lymphoblasts (Ph.D. dissertation), Oklahoma City, Okla., University of Oklahoma, 1981), particularly tumor cells relevant to liver cancer and melanoma. However, the pADI isolated from *Pseudomonas putida* failed to demonstrate its role in vivo. According to research results, the possible reasons of this about this phenomenon include that pADI almost had no bioactivity at neutral pH, and meanwhile the pADI isolated from *Pseudomonas putida* had strong immunogenicity to experimental animals and was easy to induce autoantibody synthesis after entering into the organism, and the resulted antigen-antibody immune complexes could be quickly eliminated from the blood circulation of experimental animals.

Takaku, et al (Haruo Takaku et al., In vivo anti-tumor activity of arginine deiminase purified from *Mycoplasma arginini*, Int J Cancer., 51:244-249, 1992) isolated another arginine deiminase (aADI) from *Mycoplasma arginini*. Unlike the pADI which was isolated from *Pseudomonas putida*, aADI showed the highest activity at pH of 6.0-7.5 and was very stable at neutral pH. However, pADI and ADI, which were both derived from lower microorganism species, still show solid antigenicity and thus were easy to be cleared by the circulatory system in human body.

After chemical modification (such as PEG, gelatin, polysaccharides), they can effectively block the epitope on the surface of protein, and reduce or eliminate the inherent immunogenicity of the protein, and the molecular weight of the modified protein was increased, which can extend the internal clearance rate and increase its half-life, so protein modification was a preferred method for solving the immunogenicity. Polyethylene glycol (PEG) has been recognized as a safe protein chemical modification reagent and some PEG-modified drugs have been used in clinical practice. However, PEG-modified proteins, including arginine deiminase, L-asparaginase and other enzymes will lead to a decline in or even complete loss of enzyme activity (Mehvar R, Modulation of the pharmacokinetics and pharmacodynamics of proteins by polyethylene glycol conjugation, *J. Pharm Pharmaceut Sci.*, 3:125-136, 2000). When Holtsberg F W et al (Holtsberg F W et al., Poly(ethylene glycol) (PEG) conjugated arginine deiminase: effects of PEG formulations on its pharmacological properties, *J Control Release.* 80:259-271, 2002) studied the PEG-modified ADI, they found that when the ADI was combined with 8-10 $PEG_{20000}$ molecules, only less than 50% of its enzyme activity was retained, and after further modification, when more than 20 PEG molecules were combined, its enzyme activity was almost entirely lost. Therefore, for this kind of proteins, it is necessary to optimize and balance between the activity retention and protein PEG modification in order to achieve the clinical requirements of the drugs.

SUMMARY OF THE INVENTION

The objective of the present invention is to overcome the problems of existing technology, and to provide an arginine deiminase mutant with partial lysine-deficient (ADI-Lys⁻) and preparation and application thereof.

Conventional PEG-modification not only leads to a decline in the activity of the modified proteins, but also results in inhomogenous products due to inability to control the modification sites. When Wang Y S et al (Wang Y S et al., Structural and biological characterization of pegylated recombinant interferon alpha-2b and its therapeutic implications, *Adv Drug Deliv Rev.*, 54:547-570, 2002) studied the PEG-modification of recombinant human interferon α2a (IFNα2a), they found that when using 12 KD succinimidyl carbonate PEG (SC-PEG) for modification, there would be a total of 14 chemical groups within the IFNα2a molecules, such as N-terminal amino, Lys, His and so on could be modified. For mono-modified PEG-IFNα2a, the result analysis in this article proved that the PEG-modified product of IFNα2a (referred to as PEG-IFNα2a) was actually a mixture of 14 different kinds of modified compounds each of which had a PEG molecule attached at one of 14 different sites in the original IFNα2a molecule. Furthermore, these 14 different modified products had inconsistent activities, and the relative biological activity was retained for 37% to the highest and for 6% to the lowest. Therefore, a possible proposal will be implemented through genetic mutant to minimize the number of lysine residues on the ADI, reduce the possiblility of significant loss of activity after PEG-modification and the batch differences of heterogeneous products.

After a large number of screening studies, the inventors found that some sites of lysine in the sequence of ADI were not conservative, which can be mutated to a particular amino acid with the retained enzyme activity. The first aspect of the present invention is to provide an arginine deiminase mutant, which has enzyme activity of degrading the arginine into citruline; compared with the arginine deiminase with the amino acid sequence of SEQ ID NO: 1, the amino acid sequence of which comprises one or more of the following substitutions: K9N, T; K59Q; K66R, A; K93E, A, Q; K111R, A; K119Q, L, M; K121Q, I; K122E, L; K126E, S, R; K178I, E, D; K196I, R; K209G, T, D; K243E, V, R; K249D, Q; K263N, Q; K279Y, T; K293R, H, E; K325V, I; K380T, R, E, and K406E, D, S. For example, for K9N, T substitution can be arginine deiminase containing single K9N or K9T substitution, or containing combination of one or more of K59Q; K66R, A; K93E, A, Q; K111R, A; K119Q, L, M; K121Q, I; K122E, L; K126E, S, R; K178I, E, D; K196I, R; K209G, T, D; K243E, V, R; K249D, Q; K263N, Q; K279Y, T; K293R, H, E; K325V, I; K380T, R, E and K406E, D, S substitutions with K9N or K9T substitution.

More preferably, the amino acid sequence of the arginine deiminase mutant contains K9N, K59Q, K66R, K93E, K111R, K119Q, K121Q, K122E, K126E, K178I, K196I, K209G, K243E, K249D, K279Y substitutions. Preferably, the arginine deiminase mutant has the amino acid sequence of SEQ ID NO: 2 or SEQ ID NO: 3.

The embodiments of the present invention enumerate the mutants containing K9N+K59Q+K66R+K93E+K111R+K119Q+K121Q+K122E+K126E+K178I+K196I+K209G+K243E+K249D+K279Y substitutions and each of these single substitutions. In view of retained near full activity of the ADI mutant containing these substitutions simultaneously or solely, those skilled in the art can get to know that these substitutions would not affect the bioactivity of ADI, whether one or more of the above substitutions occurred. So the ADI mutants containing one or more of those combined substitutions still can retain the enzyme activity of degrading arginine.

Further, the ADI mutant is modified by a polymer with low immunogenicity or no immunogenicity to obtain a polymer-ADI mutant with low immunogenicity or no immunogenicity.

The polymer with no immunogenicity can be natural sources, such as gelatin and dextran, or can also be synthetic, such as polyethylene glycol.

In the embodiment of the present invention, polyethylene glycol has a molecular weight from about 5,000 to 40,000, preferably about from 20,000 to 40,000, most preferably 20,000. The above mentioned polymers can be combined with the $\epsilon$-amino and N-terminal $\alpha$-amino of Lys in the sequence of ADI mutants through linking groups. These linking groups can be any biocompatible groups, including but not limited to: EDC, glutaric dialdehyde, ester group, aldehyde group, amido, carbamate group, and maleimide. In the embodiments of the invention, the biocompatible group can be hydroxysuccinimide or aldehyde group.

Adopting the method of the present invention, the above mentioned polymers can be covalently attached with the $\epsilon$-amino of all Lys and N-terminal $\alpha$-amino in the sequence of ADI mutants through linking groups, after modified by linear $PEG_{20000}$ (attached with about 11 $PEG_{20000}$ molecules), the ADI mutant with sequence of SEQ ID NO: 2 had enzyme activity of 17 U/mg and activity retention rate of 55%, which were far higher than the activity of the raADI (without mutation) modified under the same conditions, for the detail please refer to Embodiment 5.

The second aspect of the present invention provides a polynucleotide which codes the above ADI mutant.

Further, the polynucleotide has the nucleotide sequence of SEQ ID NO: 5.

The third aspect of the invention provides an expression vector containing the above polynucleotide sequence.

The methods known to those skilled in the art can be used to build a recombinant expression vector containing the coding sequence of ADI mutant and suitable transcription/translation control signals. These methods include in vitro recombination DNA techniques, DNA synthesis technique, and in vivo recombinant expression technology, etc. The above mentioned DNA sequence can be effectively connected to the appropriate promoter of the expression vector to direct the mRNA synthesis. The recombinant expression vectors can be bacterial plasmid, phage, yeast plasmid, plant cell viruses, mammalian cell virus like adenovirus and retrovirus, and other vectors well-known in the field. In addition, the expression vectors preferably contain one or more selective marker gene to provide the phenotypic characters of host cells for selection and transformation. The embodiments of the present invention concretely present pET39b as vector.

The fourth aspect of the present invention provides a recombinant host cell which contains the above mentioned expression vector, or the chromosome is integrated with the above mentioned polynucleotide.

Host cell can be prokaryocytes like bacterial; or eukaryotic expression system like yeast cells; or mammalian cells. Representative examples include: *E. coli, Streptomyces*; fungal cells like yeast; CHO and so on. Transformation of host cells with recombinant expression vectors can be implemented by well-known conventional techniques to those skilled in the art. When the host is prokaryote like *E. coli*, the competent cell which can absorb DNA can be harvested after exponential growth phase and treated with methods like $CaCl_2$, in which the used steps are well known to those skilled in the art. If necessary, the transformation can be also carried out by electroporation method. When the host is eukaryote, the following DNA transfection methods can be selected and used: calcium phosphate co-precipitation method and conventional mechanical methods like microinjection, electroporation and liposome packaging. The embodiments of the present invention present *E. coli* BL21DE3 as host cell.

The fifth aspect of the present invention provides a method for preparing ADI mutant, which includes the following:

(1) use the recombinant expression vectors containing polynucleotide for coding ADI mutant to transform and transducer suitable host cells; (2) culture suitable host cells in suitable culture mediums; (3) separate and purify proteins from culture medium or cells.

The host cells can be cultured with conventional methods to express the ADI mutant of the present invention. According to the used host cells, the used culture medium can be selected from a variety of conventional culture mediums, and cultured under the conditions suitable for the growth of host cells. When the host cells grow to appropriate cell density, the selected promoters are induced with appropriate methods and the cells will be further cultured for some time. The recombinant polypeptide in the above methods can be expressed within the cell or on the cell membrane, or be secreted outside the cell. If necessary, the recombinant proteins can be separated and purified through various separation methods by making use of its physical, chemical and other properties. These methods are well-known to those skilled in the art. Examples of these methods include, but not limited to, conventional renaturation, protein precipitant, centrifugal, homogenization, size exclusion chromatography, ion exchange chromatography, high performance liquid chromatography and various other liquid chromatography and combinations of these methods.

The sixth aspect of the present invention provides a pharmaceutical composition, which contains safe and effective dose of ADI mutant (modified or not modified by polymer) and pharmaceutically acceptable carrier or excipients. The carrier includes (but not limited to) buffer, amino acids, sugars, water for injection, and combinations thereof. The drug formulation should be matched with the administration method. The pharmaceutical composition of the present invention can be made into injection, for example, prepared by conventional methods using normal saline or aqueous solution containing glucose and other auxiliary agents. In addition, the polymer-raADI of the present invention can be also used in conjunction with other therapeutic agents.

The seventh aspect the present invention provides an application of the above mentioned ADI mutant (modified or not modified by polymer) in the preparation of drugs for treating viral infection, tumour and Alzheimer's disease.

The therapeutic effective dose of the compound of the present invention can effectively inhibit tumor growth volume. Typically, the treatment will begin with small doses, and then the dose is gradually increased until the arginine in vivo is completely decomposed. Typically, the therapeutic dose of the compound of the present invention can be from about 5 to 30 U/kg, once every two days to about once every two weeks.

Previous reports suggest that through degradation of arginine, ADI demonstrates the effects of anti-virus (Clark Mike A., U.S. Pat. No. 7,204,980: Methods for inhibiting viral replication in vivo) and Alzheimer's disease treatment (Louw C et al., Arginine deiminases: Therapeutic tools in the etiology and pathogenesis of Alzheimer's disease, *J Enzyme Inhib Med Chem.*, 22:121-126, 2007), and the raADI-Lys⁻ and PEG-raADI-Lys⁻ prepared by the present invention have the same effects and better safety, so the raADI-Lys⁻ and PEG-raADI-Lys⁻ prepared by the present invention can be also used in these fields.

Compared with natural derived ADI, the mutants of the present invention can not only retain the original enzyme activity after renaturation, more importantly, the PEG modified mutants still have high activity retention rate and higher product homogeneity.

DESCRIPTION OF SEQUENCES

Figures 1, 2:
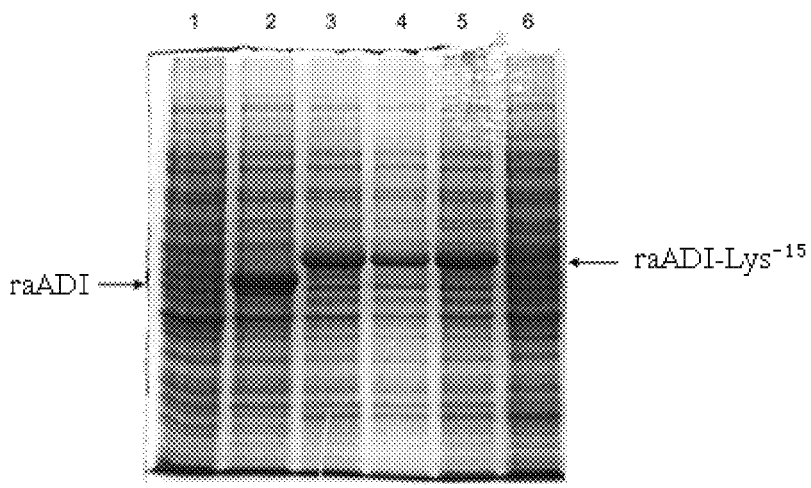
FIG. 1 shows amino acid sequence comparison between arginine deiminase derived from *mycoplasm arginini* (aADI) and arginine deiminase mutant (raADI-Lys$^{-15}$).
FIG. 2 shows expression result of recombinant arginine deiminase in *E. coli* which analyzed by SDS-PAGE. Lane 1 is blank control of uninduced recombinant ADI derived from *mycoplasma arginine* (aADI), lane 2 is raADI induced after 3 hours, lanes 3 to 5 are raADI-Lys$^{-15}$ induced after 3 hours, and lane 6 is blank control of uninduced ADI mutant (raADI-Lys$^{-15}$). The apparent molecular weight of raADI-Lys$^{-15}$ in SDS-PAGE was relatively large.
Figure 3:
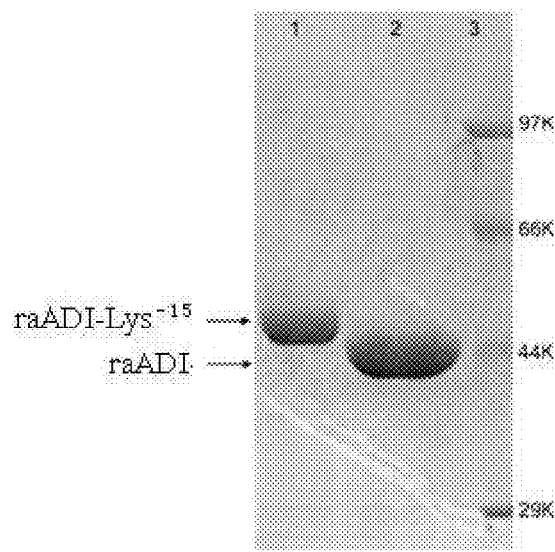
FIG. 3 shows SDS-PAGE result of the purified ADIs. Lane 1 is raADI-Lys$^{-15}$, lane 2 is raADI, and lane 3 is low molecular weight protein marker.
Figure 4:
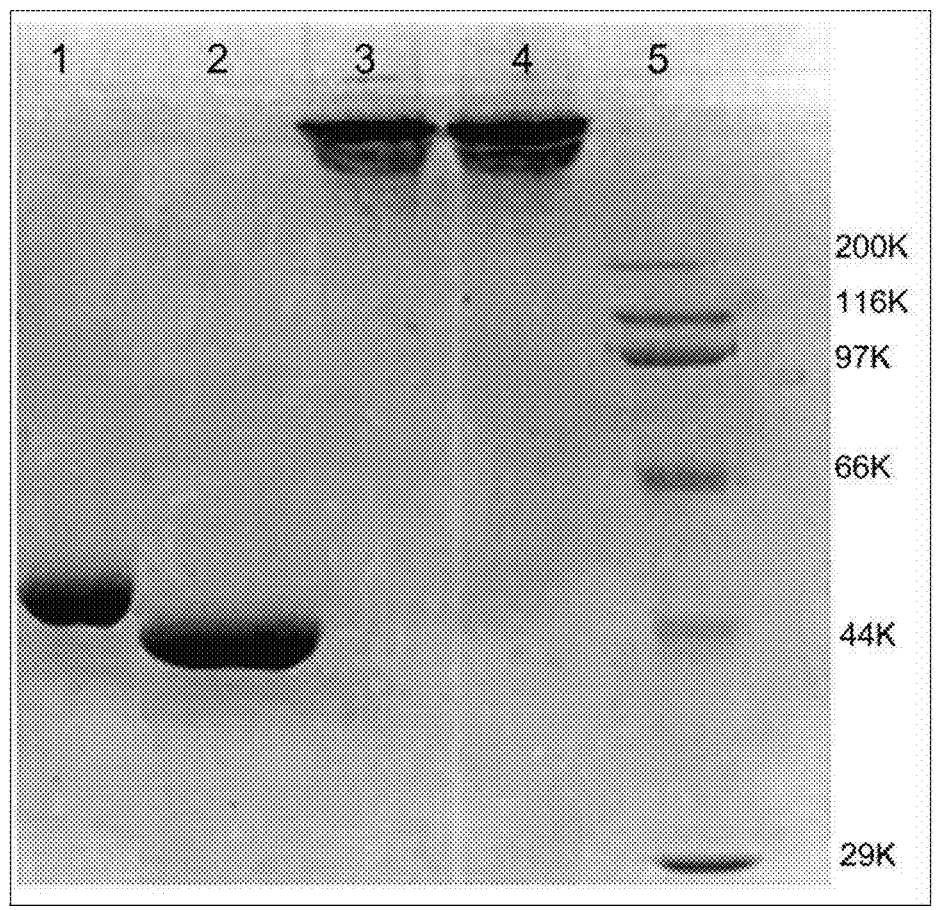
FIG. 4 shows 10% SDS-PAGE drawing of PEG-modified products of raADI and raADI-Lys$^{-15}$. Lane 1 is raADI-Lys$^{-15}$, lane 2 is natural raADI, lane 3 is mPEG$_{20000}$-raADI-Lys$^{-15}$, lane 4 is mPEG$_{20000}$-raADI and lane 5 is high molecular weight protein marker.

SEQ ID NO: 1 amino acid sequence of natural derived arginine deiminase, which is cloned from *mycoplasm arginini*.

SEQ ID NO: 2 amino acid sequence of arginine deiminase mutant (aADI-Lys$^{-15}$) containing 15 lysine substitutions.

SEQ ID NO: 3 amino acid sequence of arginine deiminase mutant containing 12 lysine substitutions.

SEQ ID NO: 4 DNA coding sequence of natural arginine deiminase which derived from *mycoplasma arginini*.

SEQ ID NO: 5 DNA coding sequence of arginine deiminase mutant containing 15 lysine substitutions.

SEQ ID NO: 6 DNA coding sequence of arginine deiminase mutant containing 12 lysine substitutions.

DETAILED DESCRIPTION OF THE EMBODIMENTS

In the disclosure of the present invention, the following abbreviations may be applied:

ADI, arginine deiminase; ADI-Lys⁻, arginine deiminase mutant with partial lysine; raADI, recombinant arginine deiminase derive from *mycoplasm arginini*; raADI-Lys$^{-15}$, recombinant arginine deiminase mutant containing 15 lysine substitutions; raADI-Lys$^{-12}$, recombinant arginine deiminase mutant containing 12 lysine substitutions; PEG, polyethylene glycol; mPEG, methoxy polyethylene glycol; mPEG$_{20000}$-raADI, arginine deiminase modified by methoxy polyethylene glycol with molecular weight of 20,000; mPEG$_{20000}$-raADI-Lys$^{-15}$, raADI-Lys$^{-15}$ modified by methoxy polyethylene glycol with molecular weight of 20,000; mPEG$_{20000}$-raADI-Lys$^{-12}$, raADI-Lys$^{-12}$ modified by methoxy polyethylene glycol with molecular weight of 20,000; NHS, N-hydroxysuccinimide; SPA, succinimidyl propionate; PB, phosphate buffer; PBS, phosphate buffer with saline.

The present invention will be further demonstrated with specific embodiments as follows. These embodiments are only used to illustrate the present invention, but not to limit the scope of the present invention.

Embodiment 1: Expression, Purification and Identification of Recombinant Arginine Deiminase Mutants 1.1 Expression and Renaturation of Recombinant Arginine Deiminase Mutants In order to obtain recombinant arginine deiminase mutant with partial lysine-deficient substitutions but retain full biological activity, the researchers of the present invention screened out an arginine deiminase mutant from arginine deiminase mutants with random point mutation in lysine sites. Compared with the aADI sequence (SEQ ID NO: 1), this ADI mutant contains partial substitutions in Lys residues sites but keep near full ADI bioactivity.

The results of sequencing showed that the amino acid sequence of the above mentioned mutant was shown in SEQ ID NO: 2 in which 15 lysines were replaced by other amino acids, and was named as raADI-Lys$^{-15}$, and the specific mutant site were as follows: K9N, K59Q, K66R, K93E, K111R, K119Q, K121Q, K122E, K126E, K178I, K196I, K209G, K243E, K249D, K279Y, respectively. The DNA coding sequence was shown in SEQ ID NO: 5, which was built by conventional methods on pET39b expression vectors and was conventionally transformed to express host bacteria BL21DE3 after identification, followed by renaturation and purification with reference to the methods of Misawa S et al (Misawa S et al., High-level expression of *Mycoplasma arginine* deiminase in Escherichia coli and its efficient renaturation as an anti-tumor enzyme, *J Biotechnol.*, 36:145-55, 1994). The methods for renaturation and purification were appropriately improved and the specific methods are summarized below:

raADI-Lys$^{-15}$ recombinant strains were cultured at 37° C., induced with 1 mM IPTG for 3 hours (see FIG. 2), and centrifuged to collect the bacteria, followed by high-pressure homogenization to broke the bacteria and centrifugation for collecting inclusion bodies and washing. 1 g of inclusion bodies were dissolved in 15 ml of growth solution (6M guanidine hydrochloride, 5 mM EDTA, 10 mM Tris, pH 8.5) and stirred at room temperature for 3 hours. 75 μl of β-mercaptoethanol was added and stirred for 30 min, then the added solution was slowly diluted by 1800 ml of renaturation solution (10 mM PB, pH to 7.2) and the renaturation solution was slowly stirred at 15° C. for 48 hours.

1.2 Purification of Recombinant Arginine Deiminase Mutants

DEAE chromatography column was fully balanced by 10 mM PB (pH 7.2) buffer and sampled with the renaturation solution, and then carried out 10 times of column bed volume of 0.5 mol/L of NaCl gradient elution to collect active raADI-Lys$^{-15}$ peak. Then the raADI-Lys$^{-15}$ target peak was added with ammonium sulfate to 1.0 mol/L. Phenyl-Spharose hydrophobic chromatography column was equilibrated by 1.0 mol/L of ammonium sulfate (containing 10 mM PB, pH7.2), and sampled with ammonium sulfate-added DEAE target peak followed by linear elution and gradient eluted with ammonium sulfate reduced from 1.0 mol/L to 0.1 mol/L. The hydrophobic chromatography target peak was desalinized through desalting column G25 to remove the ammonium sulfate, and then loaded in DEAE chromatography column again for purification to remove traces of impurities contained in samples, followed by concentration of samples by ultrafiltration. Finally, 80 mg of proteins can be obtained from per gram of inclusion bodies and after N terminal amino acid sequencing, the sequence was consistent with SEQ ID NO: 2.

raADI gene sequence (SEQ ID NO: 4) was obtained through total synthesis, like raADI-Lys$^{-15}$, which was built on pET39b expression vectors and transformed into BL21DE3 host bacteria. The steps of protein expression, renaturation and purification were the same as that of raADI-Lys$^{-15}$. Finally, 30 mg of proteins can be obtained from per gram of inclusion bodies.

1.3 Enzyme Activity Determination of Recombinant Arginine Deiminase

ADI used arginine (Arg) as substrate, and its product citrulline can be reacted with blood urinary nitrogen reagent (BUN) at high temperature of 100° C. to present red. Arg with final concentration of 100 mM and 5 μg ADI were added into the reaction system, and then complemented with 20 mM PB (pH7.2) to 500 μl. After accurate reaction at 37° C. for 30 min, 50 μl of reaction solution was added into 5 ml of blood urinary nitrogen reagent (BUN), mixed and placed into boiling water bath for 10 min, followed by determination of $OD_{540}$ with citrulline as the standard to obtain the standard curve. The blood urinary nitrogen reagent (BUN) without addition of ADI was used as control, and the content of reaction substrate citrulline (μmol) was calculated by the standard curve. Enzyme activity unit definition: one enzyme activity unit (U) is defined as ADI enzyme amount used for catalyzing 1μmol arginine to completely transform into 1 μmol citrulline in 1 min at 37° C.

ADI protein content was determined by Coomassie brilliant blue method to calculate the specific activity of ADI enzyme. Finally, the specific activities of various ADIs determined after purification were as follows:

the specific activities of raADI and raADI-Lys$^{-15}$ were about 33 U/mg and 30 U/mg, respectively.

Embodiment 2:

The mutant sites in the mutants were obtained according to embodiment 1, 48 mutant ADI proteins with single point substitution were prepared with reference to the methods in the embodiment 1, followed by testing the residue activity, and the results are as follows:

TABLE 1

Activity residue of single pointed mutated arginine deiminase mutants

| Amino acid | Amino acid after mutation | Specific activity residual rate | Amino acid | Amino acid after mutation | Specific activity residual rate |
|---|---|---|---|---|---|
| K9 | N | 90% | K196 | R | 97% |
| K9 | T | 86% | K209 | G | 90% |
| K59 | Q | 85% | K209 | T | 89% |
| K66 | R | 103% | K209 | D | 87% |
| K66 | A | 101% | K243 | E | 95% |
| K93 | E | 105% | K243 | V | 94% |
| K93 | A | 101% | K243 | R | 94% |
| K93 | Q | 96% | K249 | D | 85% |
| K111 | R | 90% | K249 | Q | 85% |
| K111 | A | 88% | K263 | N | 94% |
| K119 | Q | 105% | K263 | Q | 91% |
| K119 | L | 105% | K279 | Y | 96% |
| K119 | M | 103% | K279 | T | 93% |
| K121 | Q | 85% | K293 | R | 98% |
| K121 | I | 85% | K293 | H | 98% |
| K122 | E | 96% | K293 | E | 97% |
| K122 | L | 90% | K325 | V | 94% |
| K126 | E | 89% | K325 | I | 93% |
| K126 | S | 88% | K380 | T | 110% |
| K126 | R | 88% | K380 | R | 104% |
| K178 | I | 112% | K380 | E | 104% |
| K178 | E | 107% | K406 | E | 88% |
| K178 | D | 107% | K406 | D | 86% |
| K196 | I | 100% | K406 | S | 85% |

The results showed that the single point-mutated arginine deiminase mutants also can retain more than 85% of residue activity. In view of the results in embodiment 1 and 2, those skilled in the art can get to know that these mutational sites, no matter single substitution or multiple substitutions, almost have no effect on the activity of arginine deiminase in degrading arginine, therefore, even if partial substitutions of these 21 lysine sites occurred, the obtained mutants still can retain the enzyme activity of degrading arginine, and those skilled in this art can obtain mutants with any combination of these substitutions s according to the methods provided by the present invention.

Embodiment 3:

According to the results of embodiment 2, another segment of arginine deiminase mutant was artificially synthesized, and the amino acid and DNA sequences were shown in SEQ ID NO: 3 and SEQ ID NO: 6, respectively. Compared with SEQ ID NO: 2, this mutant sequence only had 12 Lys substitutions: K9N, K59Q, K66R, K93E, K111R, K119Q, K121Q, K122E, K126E, K178I, K196I, K209G substitutions, and was named as raADI-Lys$^{-12}$. Its expression, renaturation, purification and activity determination were the similar as the embodiment 1, and the specific activity was still about 30 U/mg. The above results proved that the 15 lysine mutations occurred in embodiment 1 can be combined at random without significantly affecting its activity.

Embodiment 4: PEG-Modification of Arginine Deiminase Mutants 100 mL 4mg/mL of raADI or raADI-Lys$^{-15}$, raADI-Lys$^{-12}$ solution (buffer system: 100 mM Bicine, pH8.0) prepared in embodiment 1 and embodiment 3 were taken and added with PEG reagent (mPEG-SPA-20KD, Beijing Kaizheng Biotech Development Co. Ltd.) at 1:60 molar ratio, stirred at room temperature for 2 hours. The modified products were purified by ultrafiltration. The resulted products from raADI and raADI-Lys$^{-15}$, raADI-Lys$^{-12}$ mutants were named as mPEG$_{20000}$-raADI and mPEG$_{20000}$-raADI-Lys$^{-15}$, mPEG$_{20000}$-raADI-Lys$^{-12}$, respectively.

Embodiment 5: Analysis and Identification of PEG-ADI

The determination of PEG modification rates of arginine deiminase was improved with reference to the methods described by Nag A et al (Nag A et al., A colorimetric assay for estimation of polyethylene glycol and polyethylene glycolated protein using ammonium ferrothiocyanate, *Anal Biochem.*, 237(2):224-231, 1996): 50 μl modified products were confirmed with enzyme digestion by proteinase K for 1 hour, and then added with 1 ml of iron thiocyanate/chloroform (1:1) reagent and shaked vigorously for half an hour to determine the absorbance value at 510 nm. The absorbance values of different concentrations of mPEG-20 kD were used for giving the standard curve and calculating the content of PEG in the samples. The determination of enzyme activity was the same as the determination of ADI activity. The results were shown in Table 2.

TABLE 2

Activity retention of PEG-modified products of arginine deiminase and arginine deiminase mutants

| | Average PEG attachment number (results of 3 batches of independent experiments) | SD value | Specific activity (U/mg) | SD value |
|---|---|---|---|---|
| $mPEG_{20000}$-raADI | 9.8 | 1.76 | 12.3 | 0.90 |
|  | 8.9 |  | 11.3 |  |
|  | 12.3 |  | 10.5 |  |
| $mPEG_{20000}$- raADI-Lys$^{-15}$ | 11.3 | 0.76 | 17.0 | 0.40 |
|  | 12.5 |  | 16.2 |  |
|  | 11.1 |  | 16.6 |  |
| $mPEG_{20000}$- raADI-Lys$^{-12}$ | 10.5 | 1.01 | 14.1 | 0.57 |
|  | 12.5 |  | 13.0 |  |
|  | 11.8 |  | 13.8 |  |

From Table 2, we can see that raADI had big deviation between different batches in average modification number and specific activity, however, the deviation between different batches of ADI mutants were relatively small, and ADI mutants retained 45-55% of the in vitro activity after combined with about 11 $mPEG_{20000}$ molecules, and the activity residual rate was significantly higher than the raADI.

Some single-mutated mutants prepared in embodiment 2 were tested for the activity residual rate after PEG modification with the same methods, and the residual activity was slightly higher than the raADI.

Embodiment 6: Drug Efficacy Experiment of H22 Engrafted Tumor Model

Figure 5:
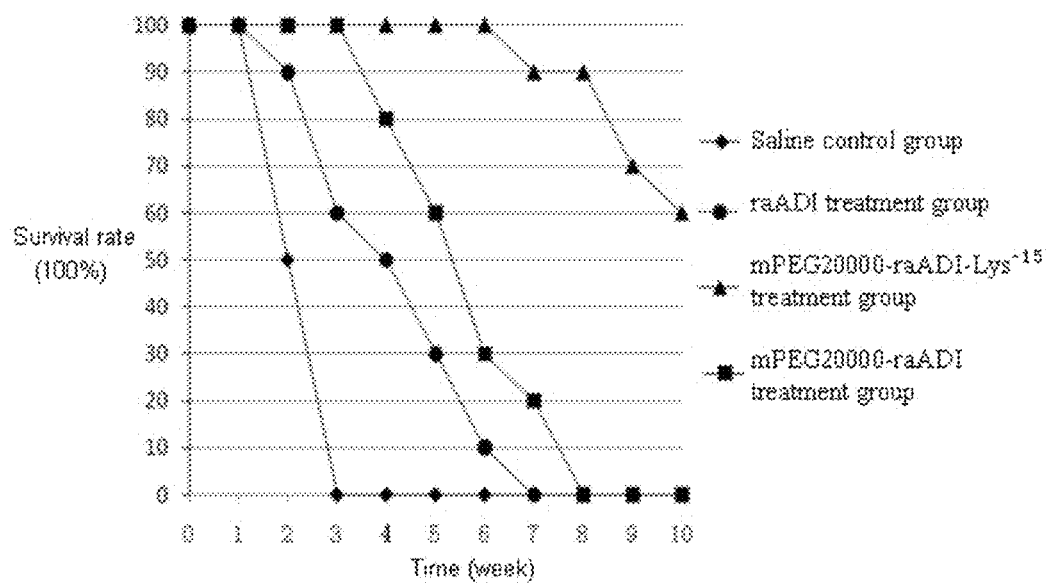
FIG. 5 shows effects of mPEG$_{20000}$-raADI-Lys$^{-15}$ and raADI on the growth of tumor-engrafted mouse. The abscissa is time (week), and the vertical axis is the survival rate (%).

In order to verify the role of inhibiting hepatocellular carcinoma of $mPEG_{20000}$-raADI-Lys$^{-15}$, 40 BALB/c-nu mice (6-week-old) were randomly selected to prepare the tumor-bearing mice. Each mouse was subcutaneously injected with $5\times10^5$ mouse liver cancer cells H22 on the back of the mouse. After bearing cancer, when the tumors grew to about the diameter of 0.5 cm, these mice were divided into four groups, respectively, $mPEG_{20000}$-raADI-Lys$^{-15}$ treatment group, $mPEG_{20000}$- raADI treatment group, raADI treatment group and saline control group. These mice were administrated once a week for two weeks. After stopping administration, the mice were continued to be fed and observed for 10 weeks. Compared with the raADI treatment group, the $mPEG_{20000}$-raADI treatment group and the saline control group, the survival rates of H22 tumor-bearing mice in the $mPEG_{20000}$-raADI-Lys$^{-15}$ treatment group were significantly increased. Until the end of the observation period, 60% of tumor-bearing mice survived and there were statistically significant differences (FIG. 5).

All literatures described herein are hereby incorporated by reference in their entirety. It should also be understood that, one skilled in the art can make various modifications or changes to the present invention after reading the above disclosures of the present invention, and these equivalent forms are still in the scope limited by the attached claims of this application.

What is claimed is:

1. An isolated arginine deiminase mutant with enzymatic activity of degrading arginine into citruline, the amino acid sequence of which comprises one or more substitutions of K9N, T; K59Q; K66R, A; K93E, A, Q; K111R, A; K119Q, L, M; K121Q, I; K122E, L; K126E, S, R; K178I, E, D; K196I, R; K209G, T, D; K243E, V, R; K249D, Q; K263N, Q; K279Y, T; K293R, H, E; K325V, I; K380T, R, E, and K406E, D, S, compared with the arginine deiminase derived from *mycoplasma arginini* with the amino acid sequence of SEQ ID NO: 1.

2. The isolated arginine deiminase mutant according to claim 1, wherein the amino acid sequence of the arginine deiminase mutant comprises one or more substitutions selected from K9N, K59Q, K66R, K93E, K111R, K119Q, K121Q, K122E, K126E, K178I, K196I, K209G, K243E, K249D, K263N, K279Y, K293R, K325V, K380T and K406E.

3. The isolated arginine deiminase mutant according to claim 1, wherein the amino acid sequence of the arginine deiminase mutant comprises K9N, K59Q, K66R, K93E, K111R, K119Q, K121Q, K122E, K126E, K178I, K196I and K209G, K243E, K249D, K279Y substitution.

4. The isolated arginine deiminase mutant according to claim 1, wherein the arginine deiminase mutant comprises the amino acid sequence as set forth in SEQ ID NO: 2 or SEQ ID NO: 3.

5. The isolated arginine deiminase mutant according to claim 1, wherein the arginine deiminase mutant is modified by polymer with low immunogenicity or no immunogenicity.

6. The isolated arginine deiminase mutant according to claim 5, wherein the polymer with low immunogenicity or no immunogenicity is selected from polyethylene glycol, gelatin or dextran, etc.

7. The isolated arginine deiminase mutant according to claim 6, wherein the polymer with low immunogenicity or no immunogenicity is polyethylene glycol with molecular weight of 5,000 to 40,000.

8. The isolated arginine deiminase mutant according to claim 7, wherein the molecular weight of polyethylene glycol is 20,000.

9. The isolated arginine deiminase mutant according to claim 5, wherein after being modified by polymer with low immunogenicity or immunogenicity-free, the activity retention rate of the arginine deiminase mutant is higher than that of arginine deiminase without mutant after modification under the same condition.

* * * * *

SEQUENCE LISTING

<160> NUMBER OF SEQ ID NOS: 6

<210> SEQ ID NO 1
<211> LENGTH: 410
<212> TYPE: PRT
<213> ORGANISM: Mycoplasma arginini

<400> SEQUENCE: 1

```
Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
                100                 105                 110
```

```
Val Val Arg Asn Phe Leu Lys Ala Lys Lys Thr Ser Arg Lys Leu Val
        115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
                180                 185                 190

Asn His Pro Lys Leu Ile Asn Thr Pro Trp Tyr Tyr Asp Pro Ser Leu
                195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
                275                 280                 285

Asn Asp Val Phe Lys Phe Trp Asp Tyr Asp Leu Val Asn Gly Gly Ala
                290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
                340                 345                 350

Tyr Leu Ala Ile Arg Pro Gly Val Val Ile Gly Tyr Ser Arg Asn Glu
                355                 360                 365

Lys Thr Asn Ala Ala Leu Glu Ala Ala Gly Ile Lys Val Leu Pro Phe
                370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 2
<211> LENGTH: 410
<212> TYPE: PRT
<213> ORGANISM: artificial sequence
<220> FEATURE:
<223> OTHER INFORMATION: amino acid sequence of arginine deiminase
      mutant with partial mutated lysine

<400> SEQUENCE: 2

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Gln Gln Phe Val Ala Glu
                50                  55                  60
```

```
Leu Arg Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Glu Leu Ile Glu
             85                  90                  95

Glu Phe Leu Glu Asp Ser Glu Pro Val Leu Ser Glu His Arg Val
            100                 105                 110

Val Val Arg Asn Phe Leu Gln Ala Gln Glu Thr Ser Arg Glu Leu Val
            115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Ile Val Arg Gln Arg Glu Thr Leu Phe Ser Arg Phe Val Phe Ser
            180                 185                 190

Asn His Pro Ile Leu Ile Asn Thr Pro Trp Tyr Tyr Asp Pro Ser Leu
            195                 200                 205

Gly Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Glu Asn Ile Val Ala Asn Asp Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Tyr Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
            370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 3
<211> LENGTH: 410
<212> TYPE: PRT
<213> ORGANISM: artificial sequence
<220> FEATURE:
<223> OTHER INFORMATION: amino acid sequence of arginine deiminase
      mutant with partial mutated lysine

<400> SEQUENCE: 3

Met Ser Val Phe Asp Ser Lys Phe Asn Gly Ile His Val Tyr Ser Glu
1                5                  10                  15
```

```
Ile Gly Glu Leu Glu Ser Val Leu Val His Glu Pro Gly Arg Glu Ile
         20                  25                  30

Asp Tyr Ile Thr Pro Ala Arg Leu Asp Glu Leu Leu Phe Ser Ala Ile
         35                  40                  45

Leu Glu Ser His Asp Ala Arg Lys Glu His Gln Gln Phe Val Ala Glu
 50                  55                  60

Leu Arg Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Glu Leu Ile Glu
             85                  90                  95

Glu Phe Leu Glu Asp Ser Glu Pro Val Leu Ser Glu Glu His Arg Val
            100                 105                 110

Val Val Arg Asn Phe Leu Gln Ala Gln Glu Thr Ser Arg Glu Leu Val
            115                 120                 125

Glu Ile Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Ile Val Arg Gln Arg Glu Thr Leu Phe Ser Arg Phe Val Phe Ser
            180                 185                 190

Asn His Pro Ile Leu Ile Asn Thr Pro Trp Tyr Tyr Asp Pro Ser Leu
        195                 200                 205

Gly Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
        290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 4
<211> LENGTH: 1233
<212> TYPE: DNA
<213> ORGANISM: Mycoplasma arginini
```

<400> SEQUENCE: 4

```
atgtctgtat ttgacagtaa atttaaagga attcacgttt attcagaaat tggtgaatta        60
gaatcagttc tagttcacga accaggacgc gaaattgact atattacacc agctagacta       120
gatgaattat tattctcagc tatcttagaa agccacgatg ctagaaaaga acacaaacaa       180
ttcgtagcag aattaaaagc aaacgacatc aatgttgttg aattaattga tttagttgct       240
gaaacatacg atttagcatc acaagaagct aaagataaat taatcgaaga attttttagaa      300
gactcagaac cagttctatc agaagaacac aaagtagttg taagaaactt cttaaaagct       360
aaaaaaacat caagaaaatt agtagaaatc atgatggcag ggatcacaaa atacgattta       420
ggtatcgaag cagatcacga attaatcgtt gacccaatgc caaacctata cttcacacgt       480
gacccatttg catcagtagg taatggtgta acaatccact acatgcgtta caaagttaga       540
caacgtgaaa cattattctc aagatttgta ttctcaaatc accctaaaact aattaacact      600
ccatggtact acgacccttc actaaaatta tcaatcgaag gtggagacgt atttatctac       660
aacaatgaca cattagtagt tggtgtttct gaaagaactg acttacaaac agttacttta       720
ttagctaaaa acattgttgc taataaagaa tgtgaattca aacgtattgt tgcaattaac       780
gttccaaaat ggacaaactt aatgcactta gacacatggc taacaatgtt agacaaggac       840
aaattcctat actcaccaat cgctaacgac gtatttaaat tctgggatta tgacttagta       900
aacggtggag cagaaccaca accagttgaa aacggattac ctctagaagg attattacaa      960
tcaatcatta caaaaaaacc agttttaatt cctatcgcag gtgaaggtgc ttcacaaatg      1020
gaaatcgaaa gagaaacaca cttcgatggt acaaactact tagcaattag accaggtgtt      1080
gtaattggtt actcacgtaa cgaaaaaaca aacgctgctc tagaagctgc aggcattaaa      1140
gttcttccat tccacggtaa ccaattatca ttaggtatgg gtaacgctcg ttgtatgtca      1200
atgcctttat cacgtaaaga tgttaagtgg taa                                   1233
```

<210> SEQ ID NO 5
<211> LENGTH: 1233
<212> TYPE: DNA
<213> ORGANISM: artificial sequence
<220> FEATURE:
<223> OTHER INFORMATION: DNA coding sequence of arginine deiminase mutant with partial mutated lysine

<400> SEQUENCE: 5

```
atgtctgtat ttgacagtaa atttaacgga attcacgttt attcagaaat tggtgaatta        60
gaatcagttc tagttcacga accaggacgc gaaattgact atattacacc agctagacta       120
gatgaattat tattctcagc tatcttagaa agccacgatg ctagaaaaga acaccagcaa       180
ttcgtagcag aattacgtgc aaacgacatc aatgttgttg aattaattga tttagttgct       240
gaaacatacg atttagcatc acaagaagct aaagatgaat taatcgaaga attttttagaa      300
gactcagaac cagttctatc agaagaacac cgtgtagttg taagaaactt cttacaggct       360
caggaaacat caagagaatt agtagaaatc atgatggcag ggatcactaa atacgattta       420
ggtatcgaag cagatcacga attaatcgtt gacccaatgc caaacctata cttcacacgt       480
gacccatttg catcagtagg taatggtgta acaatccact acatgcgtta catcgttaga       540
caacgtgaaa cattattctc aagatttgta ttctcaaatc accctatcct aattaacact       600
ccatggtact acgacccttc actaggttta tcaatcgaag gtggagacgt atttatctac       660
aacaatgaca cattagtagt tggtgtttct gaaagaactg acttacaaac agttacttta       720
```

-continued

```
ttagctgaaa acattgttgc taatgacgaa tgtgaattca aacgtattgt tgcaattaac    780
gttccaaaat ggacaaactt aatgcactta gacacatggc taacaatgtt agactacgac    840
aaattcctat actcaccaat cgctaacgac gtatttaaat tctgggatta tgacttagta    900
aacggtggag cagaaccaca accagttgaa aacggattac ctctagaagg attattacaa    960
tcaatcatta acaaaaaacc agttttaatt cctatcgcag gtgaaggtgc ttcacaaatg   1020
gaaatcgaaa gagaaacaca cttcgatggt acaaactact tagcaattag accaggtgtt   1080
gtaattggtt actcacgtaa cgaaaaaaca aacgctgctc tagaagctgc aggcattaaa   1140
gttcttccat tccacggtaa ccaattatca ttaggtatgg gtaacgctcg ttgtatgtca   1200
atgcctttat cacgtaaaga tgttaagtgg taa                                1233

<210> SEQ ID NO 6
<211> LENGTH: 1233
<212> TYPE: DNA
<213> ORGANISM: artificial sequence
<220> FEATURE:
<223> OTHER INFORMATION: DNA coding sequence of arginine deiminase
      mutant with partial mutated lysine

<400> SEQUENCE: 6
atgtctgtat ttgacagtaa atttaacgga attcacgttt attcagaaat tggtgaatta     60
gaatcagttc tagttcacga accaggacgc gaaattgact atattacacc agctagacta    120
gatgaattat tattctcagc tatcttagaa agccacgatg ctagaaaaga acaccagcaa    180
ttcgtagcag aattacgtgc aaacgacatc aatgttgttg aattaattga tttagttgct    240
gaaacatacg atttagcatc acaagaagct aaagatgaat taatcgaaga attttttagaa    300 gactcagaac cagttctatc agaagaacac cgtgtagttg taagaaactt cttacaggct    360
caggaaacat caagagaatt agtagaaatc atgatggcag ggatcactaa atacgattta    420
ggtatcgaag cagatcacga attaatcgtt gacccaatgc caaacctata cttcacacgt    480
gacccatttg catcagtagg taatggtgta acaatccact acatgcgtta catcgttaga    540
caacgtgaaa cattattctc aagatttgta ttctcaaatc accctatcct aattaacact    600
ccatggtact acgacccttc actaggttta tcaatcgaag gtggagacgt atttatctac    660
aacaatgaca cattagtagt tggtgtttct gaaagaactg acttacaaac agttactta    720 ttagctaaaa acattgttgc taataaagaa tgtgaattca aacgtattgt tgcaattaac    780
gttccaaaat ggacaaactt aatgcactta gacacatggc taacaatgtt agacaaggac    840
aaattcctat actcaccaat cgctaacgac gtatttaaat tctgggatta tgacttagta    900
aacggtggag cagaaccaca accagttgaa aacggattac ctctagaagg attattacaa    960
tcaatcatta acaaaaaacc agttttaatt cctatcgcag gtgaaggtgc ttcacaaatg   1020
gaaatcgaaa gagaaacaca cttcgatggt acaaactact tagcaattag accaggtgtt   1080
gtaattggtt actcacgtaa cgaaaaaaca aacgctgctc tagaagctgc aggcattaaa   1140
gttcttccat tccacggtaa ccaattatca ttaggtatgg gtaacgctcg ttgtatgtca   1200
atgcctttat cacgtaaaga tgttaagtgg taa                                1233
```